United States Patent [19]

Hansen et al.

[11] 4,284,412

[45] Aug. 18, 1981

[54] METHOD AND APPARATUS FOR AUTOMATED IDENTIFICATION AND ENUMERATION OF SPECIFIED BLOOD CELL SUBCLASSES

[75] Inventors: W. Peter Hansen, Middleboro; Robert A. Hoffman, Mansfield, both of Mass.

[73] Assignee: Ortho Diagnostics, Inc., Raritan, N.J.

[21] Appl. No.: 57,482

[22] Filed: Jul. 13, 1979

[51] Int. Cl.$^3$ .................. G01N 33/48; G01N 21/64
[52] U.S. Cl. .................................... 23/230 B; 23/915; 250/432 R; 250/459; 250/565; 356/39; 422/81; 422/82; 424/8; 424/12
[58] Field of Search .................. 23/230 B, 915; 424/8, 424/12; 356/36, 39; 250/565, 432 R, 458, 459, 461 B, 574; 422/81, 82; 435/7

[56] References Cited

U.S. PATENT DOCUMENTS

| | | | |
|---|---|---|---|
| 3,661,460 | 5/1972 | Elking et al. | 356/36 |
| 3,679,312 | 7/1972 | Mansberg | 356/36 |
| 3,740,143 | 6/1973 | Groner | 356/39 |
| 3,781,112 | 12/1973 | Groner | 356/39 |
| 3,824,402 | 7/1974 | Mullaney | 250/565 |
| 3,883,247 | 5/1975 | Adams | 356/39 |
| 3,896,307 | 7/1975 | Trowe | 356/39 |
| 3,905,767 | 9/1975 | Morris | 23/230 B |
| 3,916,205 | 10/1975 | Kleinerman | 356/39 |
| 3,990,851 | 11/1976 | Gross et al. | 23/230 B |
| 3,996,345 | 7/1976 | Ullman | 23/230 B |
| 4,070,113 | 1/1978 | Frazer | 356/39 X |
| 4,072,421 | 2/1978 | Coyne | 356/39 |
| 4,099,917 | 7/1978 | Kim | 23/230 B |
| 4,100,416 | 7/1978 | Hirschfeld | 356/39 X |
| 4,101,276 | 7/1978 | Anderson | 23/230 B |
| 4,125,828 | 11/1978 | Resnick | 356/39 X |
| 4,133,873 | 1/1979 | Noller | 424/8 |

OTHER PUBLICATIONS

Strelkauskas et al., J. Immunology 120, 1278, 1978.
Salzman et al., "Cell Class. by Laser Light Scatter.: Ident. and Seperat. of Unstained Leukocytes, " ACTA Cytologica 19, 374 (1975).
Evans et al., Journal Immunology 120, 1423 (1978).
Reinherz et al., "A Monoclonal Antibody with Select. React. with Funct. Mature Human Thymocytes . . . ", Jour. Immuno., In Press 1979.
Reinherz et al., "Sep. of Func. Subsets of Human T Cells by a Monoclonal Antibody", PNAS, In Press 1979.
Moretta et al., "Subpopulations of Human T Cells Ident. by Receptors for Immunoglobulins and Mitogen Respon.", J. Immuno. 117, 2171, 1976.
Reinherz et al., "Monoclonal Antibodies Defin. Distint. Human T Cell Surface Antigens", Science, In Press, 1979.

Primary Examiner—Ronald Serwin
Attorney, Agent, or Firm—Audley A. Ciamporcero, Jr.

[57] ABSTRACT

Specified subclasses of blood cells, such as of lymphocytes, are automatically identified based on utilization of antigenic determinants on the cell surface, their reactivity with antibodies which fluoresce under known circumstances, and utilization of principles of flow cytometry. A blood sample is first incubated with a reagent including antibodies to the lymphocyte subclass to be identified, the antibodies being directly or indirectly made fluorescently responsive to particular light (e. g. argon ion laser). The sample is illuminated, a cell at a time, by such focused coherent light, and forward light scatter, right angle light scatter, and fluorescence are detected and used to identify and enumerate cells of the specified subclass.

14 Claims, 8 Drawing Figures

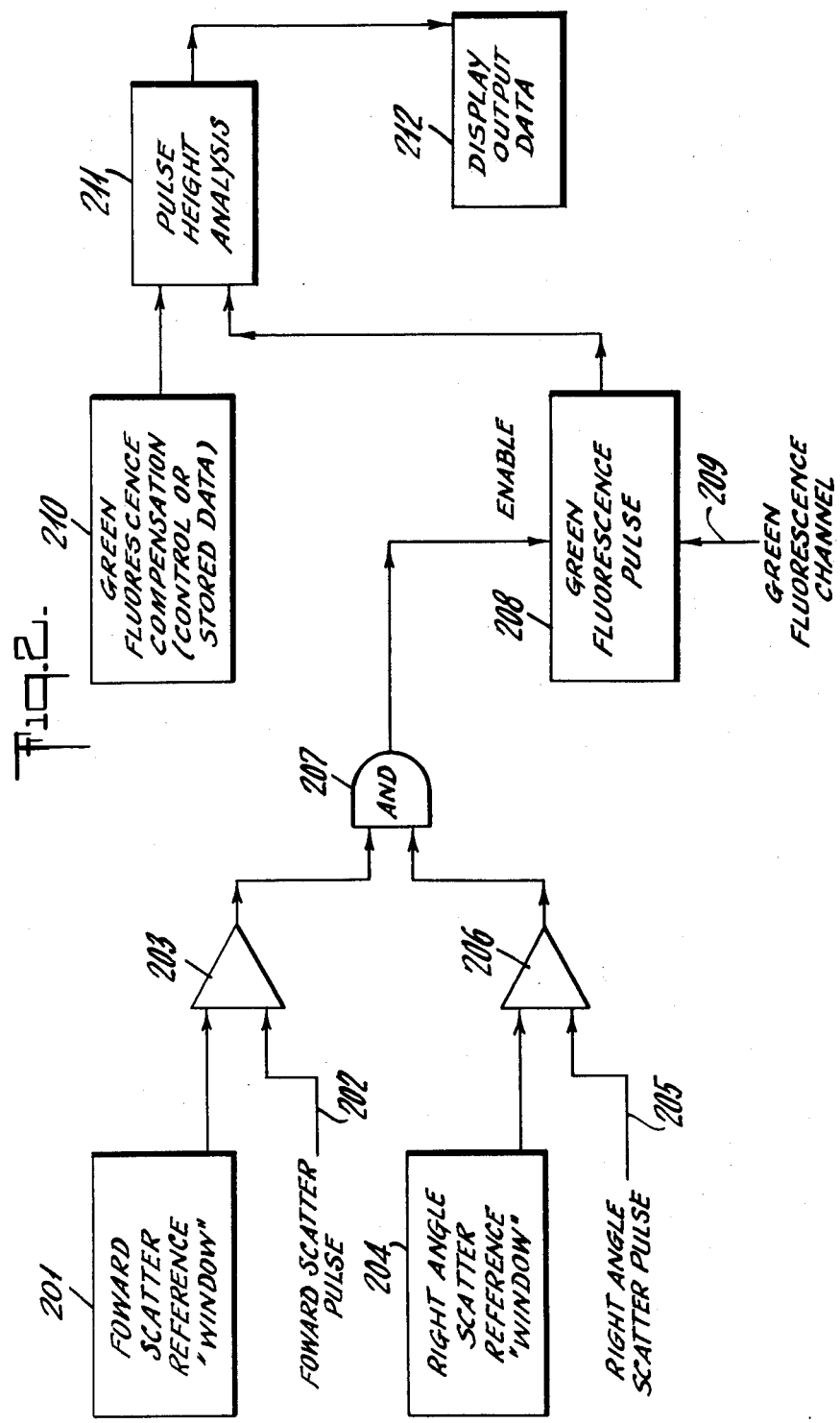

METHOD AND APPARATUS FOR AUTOMATED IDENTIFICATION AND ENUMERATION OF SPECIFIED BLOOD CELL SUBCLASSES

FIELD OF THE INVENTION

This invention relates to automated hematology instruments and procedures, and more particularly to identification and enumeration of specified subclasses of blood cells, such as certain types of lymphocytes.

BACKGROUND AND PRIOR ART

Lymphocyte population in blood is defined by a number of subclasses which play distinct roles in the immune response. For example, the relative number of lymphocytes in various subclasses is likely to change in disease states. Hence, enumeration and identification of cells of the various subclasses yields an indication not only of the constituency of the blood in particular, but generally with respect to the relative well being of the organism.

It is known that at least several particular subclasses of functionally distinct lymphocytes can be identified on the basis of antigenic determinants on the cell surface. In particular, considerable academic and clinical interest has occurred for T-lymphocytes. Among others, T-lymphocytes are characterized by particular, identifiable antigenic determinants on their surface, which distinguish the cells of that subclass from other blood cells and from the cells of other lymphocyte subclasses. Hence, interest is high in identifying and producing reagents which include antibodies which are selectively reactive with the lymphocyte subclasses of interest.

It should be understood that there are two principal classes of lymphocytes involved in the immune system of humans and animals. The first of these (the thymus-derived cell or T cell) is differentiated in the thymus from haemopoietic stem cells. While within the thymus, the differentiating cells are termed "thymocytes." The mature T cells emerge from the thymus and circulate between the tissues, lymphatics, and the bloodstream. These T cells form a large proportion of the pool of recirculating small lymphocytes. They have immunological specificity and are directly involved in cell-mediated immune responses (such as graft rejection) as effector cells. Although T cells do not secrete humoral antibodies, they are sometimes required for the secretion of these antibodies by the second class of lymphocytes discussed below. Some types of T cells play a regulating function in other aspects of the immune system. The mechanism of this process of cell cooperation is not yet completely understood.

The second class of lymphocytes (the bone marrow-derived cells or B cells) are those which secrete antibody. They also develop from haemopoietic stem cells, but their differentiation is not determined by the thymus. In birds, they are differentiated in an organ analogous to the thymus, called the Bursa of Fabricius. In mammals, however, no equivalent organ has been discovered, and it is thought that these B cells differentiate within the bone marrow.

It is now recognized that T cells are divided into at least several subtypes, termed "helper", "suppressor", and "killer" T cells, which have the function of (respectively) promoting a reaction, suppressing a reaction, or killing (lysing) foreign cells. These subclasses are well understood for murine systems, but they have only recently been described for human systems. See, for example, R. L. Evans, et al., *Journal of Experimental Medicine*, Volume 145, 221–232, 1977; and L. Chess and S. F. Schlossman—"Functional Analysis of Distinct Human T Cell Subsets Bearing Unique Differentiation Antigens", in "Contemporary Topics in Immunobiology", O. Stutman, Editor, Plenum Press, 1977, Volume 7, 363–379.

The ability to identify or suppress classes or subclasses of T cells is important for diagnosis or treatment of various immunoregulatory disorders or conditions. For example, certain leukemias and lymphomas have differing prognosis depending on whether they are of B cell or T cell origin. Thus, evaluation of the disease prognosis depends upon distinguishing between these two classes of lymphocytes. See, for example, A. C. Aisenberg and J. C. Long, *The American Journal of Medicine*, 58:300 (March, 1975); D. Belpomme, et al., in "Immunological Diagnosis of Leukemias and Lymphomas", S. Thierfelder, et al., eds, Springer, Heidelberg, 1977, 33–45; and D. Belpomme, et al., British Journal of Haematology, 1978, 38, 85. Certain disease states (e.g. juvenile rheumatoid arthritis and certain leukemias) are associated with an imbalance of T cell subclasses. It has been suggested that autoimmune diseases generally are associated with an excess of "helper" T cells or a deficiency of certain "suppressor" T cells, while malignancies generally are associated with an excess of "suppressor" T cells. In certain leukemias, excess T cells are produced in an arrested stage of development. Diagnosis may thus depend on the ability to detect this imbalance or excess. See, for example, J. Kersey, et al., "Surface Markers Define Human Lymphoid Malignancies with Differing Prognoses" in *Haematology and Blood Transfusion*, Volume 20, Springer-Verlag, 1977, 17–24, and references contained therein. Recently, monoclonal antibody techniques have been utilized to produce large quantities of highly purified antibody to various lymphocyte subclasses. Utilizing such antibodies, it has proven feasible to assay an individual's lymphocytes to determine the relative numbers of cells in various subclasses. Further, utilizing direct or indirect techniques, the antibodies may be fluorescently tagged, thereby rendering the samples under consideration amenable to flow cytometric analysis.

Conventional immunofluorescence techniques presently include the physical isolation of the lymphocytes from other leukocytes as a preliminary step. This step eliminates the possibility that non-specifically stained monocytes or granulocytes might be counted as specifically stained lymphocytes. This initial lymphocyte isolation step is long and arduous, however, in fact much longer than the relatively simple steps of staining or analyzing the lymphocytes. Clearly, in the clinical arena, wherein there exists a considerable premium on rapid, repetitive analyses, the necessity of isolating the lymphocytes from other leukocytes is a virtually insurmountable impediment. Furthermore, even for those research applications wherein time is at less of a premium, the initial lymphocyte isolation step involves the risk of loss of some lymphocytes, during removal of monocytes and granulocytes, which introduces uncertainty and inaccuracy to the subsequent analysis. Correspondingly, failure completely to eliminate other blood cells from the lymphocytes to be isolated introduces considerable risk of error, and the presence of such other cells may well cause errors in the subsequent analysis.

It is, accordingly, a primary object of the present invention to provide a method and apparatus for identifying and enumerating specific subclasses of lymphocytes, while avoiding the necessity for prior separation of lymphocytes from other blood cells. It is an associated object to provide such methods and apparatus for other types of blood cells which involve similar antigenic characteristics.

Correspondingly, it is an object to provide methods and apparatus which are considerably faster than present techniques, and which substantially obviate faulty analysis attendant to artifact data from other cells, or loss of data through loss of lymphocytes from the sample. Further, it is an object to provide such methods and apparatus wherein the speed and relative simplicity involved renders lymphocyte subclass identification and enumeration a viable clinical tool.

SUMMARY OF THE PRESENT INVENTION

The present invention involves select modification of conventional flow cytofluorometric apparatus in terms of optics and signal processing, whereupon selective immunofluorescent staining (direct or indirect) of the subclass in interest may be utilized, and the entire blood sample (as desired, either buffy coat or anticoagulated whole blood) is analyzed a cell at a time.

In a preferred embodiment, one of the right angle fluorescence channels of a flow cytofluorometric apparatus is adapted to serve as a wavelength specific sensor for right angle scatter. A sample of whole blood or buffy coat is incubated to allow specific antigens on the surface of the lymphocytes of the subclass in interest to combine with an antibody having a predetermined fluorescence response to given illumination (e.g. focused coherent light from an argon ion laser), whereby cells of the subclass in interest themselves effectively become fluorescent responsive to such incident light. The cells of the sample are then passed through the flow channel of a flow cytometer having capacity to monitor forward light scatter, as well as right angle light scatter and fluorescence. Certain forward scatter conditions, when noted, are used in conjunction with right angle light scatter conditions, in order to gate detected fluorescence. Upon detection of specific fluorescence of a given color (e.g. green), an output signal is produced to indicate the occurrence of a lymphocyte of the given subclass. Thereupon, this data may be duly stored and/or displayed (e.g. on some form of histogram). Further, as is known in the art, cell sorting techniques may be utilized to physically isolate the lymphocyte cells of the given subclass.

DESCRIPTION OF THE DRAWINGS

FIG. 2 shows a schematic diagram of signal processing apparatus, whereby the apparatus of the type shown in FIG. 1 may be utilized, in conjunction with the principles of the present invention, to identify and enumerate specific subclasses of lymphocytes.

BEST MODE FOR CARRYING OUT THE INVENTION

Figure 1:
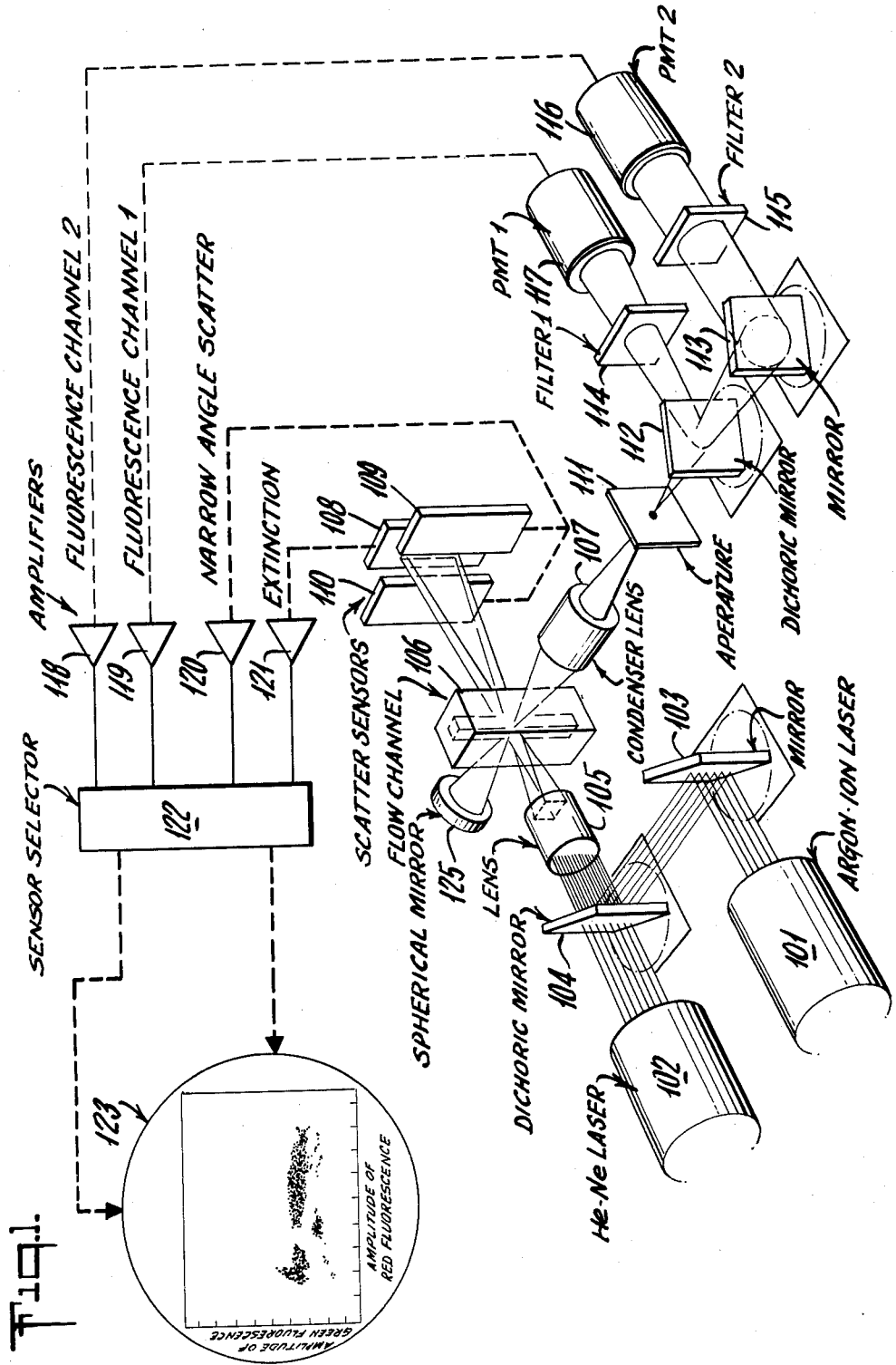
FIG. 1 shows a stylized version of a commercially available flow cytofluorometric apparatus.

Referring first to FIG. 1, there is shown a stylized functional and structural representation of apparatus which may be utilized in accordance with the principles of the present invention. In fact, the apparatus of FIG. 1 depicts a particular system available commercially under the trade designation CYTOFLUOROGRAPH, ® which is sold by Ortho Instruments, 410 University Avenue, Westwood, Mass. 02090. The apparatus of FIG. 1 incorporates the principles of flow cytometry for cell analysis, and includes capacity for sensing cell fluorescence response to specific types of illumination.

Focal to the FIG. 1 apparatus is a flow channel 106, wherein cells in liquid suspension are passed, in single file and at a rapid rate (e.g. 2500 cells per second) through a sensing zone. The sensing zone is defined by the intersection of cell flow and an incident light beam, typically focused coherent light from a gas laser. As the cell passes through the sensing zone, it interacts with incident light in a variety of ways. Some light, of course, is absorbed by the cell, other light is scattered at relatively narrow angles to the axis of incident light, and still other light is scattered at angles quite divergent from the axis of incident light, for example at right angles to the incident light. Furthermore, depending upon the nature of the cell itself, and any dyeing or staining to which the cell may previously have been subjected, fluorescence emissions may also occur.

Accordingly, photosensors located at various orientations with respect to the cell stream and the incident laser light permit detection of a unique set of responses for each given type of cell. Thus FIG. 1 includes an argon ion laser 101 and a helium neon laser 102, with the coherent light emitted by each being variously deflected via mirrors 103 and 104 and a lens 105 to the sensing zone of the flow channel 106. As is known in the art, the cell sample stream is carried in laminar fashion within a flowing fluid sheath, to insure that but a single cell will be illuminated in the sensing zone at a given time. Hence, as each cell is illuminated by light from the lens, interaction of the cell with the light may be sensed.

As shown in FIG. 1, an extinction sensor 108 detects the amount of light blocked by the cell, and forward light scatter is detected by photosensors 109 and 110 approximately in a cone of half-angle 20°. Electrical signals generated by the sensors 108, 109 and 110 are coupled to amplifiers 120 and 121, which present electrical signals of suitable amplitude and the like for subsequent analysis and/or display.

In the apparatus of FIG. 1, light which is emitted from the cell by virtue of a fluorescence response is sensed at right angles both to the direction of cell flow and to the axis of incident light. A spherical mirror 125 and a condenser lens 107 collects this light approximately in a cone of half-angle 20°, and couples this light through an aperture 111, successively to a dichroic mirror 112 and to a second mirror 113. A first color filter 114 (e.g. to pass relatively long wavelength light) conveys select light from the dichroic mirror 112 to photosensor 117 (e.g. a photomultiplier tube). A second filter 115 selectively passes light of a different color (e.g. relatively short wavelength light) from the second mirror 113 to a second photosensor 116. Electrical signals from sensors 116 and 117, in the form of pulses corresponding to light from respective cells, are coupled to amplifiers 118 and 119, thereby also to produce signals which are adapted for suitable processing.

As shown in the FIG. 1 embodiment, a sensor selector 122 generates output histograms utilizing signals from the amplifiers 118 through 121. For example, one useful form of output is a plot of amplitude of red fluorescence, from sensor 117, against amplitude of green fluorescence, from sensor 116. Such a histogram is shown at display 123, with each point on the histogram representing an individual cell. Clusters or aggregates of indicators on the histogram represent groups of cells of similar type. Quite evidently, those of ordinary skill in the art find it useful variously to generate histograms of narrow forward angle scatter versus intensity of green fluorescence, narrow forward angle scatter versus axial light extinction, and so forth.

In accordance with known applications of the apparatus of FIG. 1, the so-called first fluorescence channel 119, from sensor 117, while principally used to measure long wave length fluorescence, is also under certain circumstances useful for detecting wide angle scatter. Such is the case in accordance with the principles of the present invention, and in order to accentuate this factor, it is preferred that the conventional red filter block 114 be replaced with filters appropriate for directing to sensor 117 the blue laser light from laser 101 which is scattered at right angles to the axis of incident light from lens 105. Adaptation of the design parameters of the photomultiplier 117 and amplifier 119 may correspondingly be required, in accordance with the abilities of those of ordinary skill in the art, in order to produce signals of suitable characteristics for subsequent processing.

FIG. 2 sets forth a block diagramatic version of preferred signal processing aspects in accordance with the principles of the present invention, but that apparatus may perhaps be better understood upon detailed consideration of the following theoretical and method aspects of the present invention.

Proper preparation of a blood sample in accordance with the principles of the present invention essentially involves incubation of the sample with an antibody to the subclass of interest, which possesses the requisite characteristic of emitting fluorescent light upon illumination by the incident laser light. In one approach, whole blood from normal human donors is anticoagulated (for example with EDTA), centrifuged, and the buffy coat is isolated. Alternatively, anticoagulated whole blood is utilized. Incubation with suitable antibody is accomplished, whereupon red cells are lysed from the sample in conventional fashion. Thereupon, assuming the initial antibody was properly fluorescently active, the sample is ready for dilution and flow cytofluorometric analysis. In the event that indirect immunofluorescent staining is involved, a second incubation is conducted with a second antibody to the first antibody, which in turn has the requisite fluorescent characteristics.

As the sample is passed through the flow channel and illuminated, the optical parameters of extinction, forward light scatter, right angle scatter and fluorescence are simultaneously detected, but from the signal processing standpoint, the significance of the various parameters is considered on a relative priority basis. That is, both the forward narrow angle pulse (optionally but not necessarily also including the extinction signal) and the right angle scatter pulse, must be within respective ranges for the use of the green fluorescent signal to be actuated. Thereupon, after correction for spurious fluorescence emanations from uncombined antibodies or the like, presence of a green fluorescence pulse indicates presence of a lymphocyte cell of the specified subclass. This approach works because the "window" for forward scatter has the effect of discriminating leukocytes from platelets, partially lysed red cells, and spurious debris in the solution, and the "window" with respect to right angle scatter discriminates lymphocytes from monocytes and granulocytes. Detection of a cell having narrow angle scatter and right angle scatter pulses within the respective windows thereby effectively corresponds to detection of the presence of a lymphocyte.

The primary indicator of the desired subclass of lymphocyte is fluorescence of the particular color. Of course, if the sample includes spurious indicators, it will be necessary to account for the effect of such indicators. One such indicator includes fluorescing molecules in solution, which may be eliminated by washing the sample prior to flow cytometric analysis. Another class of spurious indicator is produced by non-specific binding of fluorescent antibodies to cells. One approach to either type of indicator (or both) is to maintain on hand a control material, which models the effect of spurious or artifact fluorescence data. Another is to maintain in the instrument data corresponding to the response of such control. Clearly, a true reading may be obtained by compensating the actual detected sample signals by introduction of the control factor, typically by combining (e.g., subtraction or deconvolution) the response of the control with the actual gated fluorescence signal. In similar fashion, control samples or control data may be utilized to correct for a variety of conditions which may be detected by those of ordinary skill in the art.

Referring, then, to FIG. 2, there is shown a functional block diagram embodying procedures in accordance with the principles of the present invention. In FIG. 2, a forward scatter reference "window" is represented at 201, and a right angle scatter reference "window" at 204. These reference values may be maintained as simply as by fixed or adjustable potientometers, or by as elaborate and esoteric approaches as stored program control which accounts for various environmental factors, variables associated with the type or amount of processing involved in the blood being sampled, or the like. In any event, the "windows" at 201 and 204 respectively define amplitude ranges wherein corresponding forward scatter or right angle scatter pulses define possible leukocytes. The forward scatter pulse signal 202, such as may be produced at amplifier 120 of FIG. 1 from the narrow angle photosensors 109 and 110, is coupled to a comparator 203, which provides an enabling signal to AND-gate 207 when the associated pulse at 202 falls within the window defined at 201. Simarly, the right angle scatter pulse signal at 205 is coupled to yet another comparator 206, the other input of which is provided with the reference "window" for right angle scatter from 204. Again, when the right angle scatter pulse at 205 falls within the right angle scatter window, an enabling signal is conveyed from comparator 206 to AND-gate 207. Hence, upon coincidence of occurrence of a forward scatter pulse within the forward scatter reference window, and a right angle pulse within the right angle scatter window, AND-gate 207 enables a determination at 208 which serves to identify the occurrence of a green fluorescent pulse from the green fluorescence channel 209 (e.g. from amplifier 118 of the FIG. 1 apparatus).

Next, a pulse height analyzer 211 is shown, which variously compensates data from the green fluorescence channel, and produces suitable display and output data. As previously stated, the compensation may be as simple as subtraction of a certain amount of intensity due to spurious but anticipated fluorescent signals, or may be as elaborate as the generation of data by prior or subsequent analysis of a control sample. Generally, the pulse height analysis at 211 constitutes suitable amplification, filtering, and signal processing in accordance with the conventional approaches such as are well within the capability of those of ordinary skill in the art. The display or generation of output data at 212 involves generation of suitable histograms or the like which are also within the capability of those of ordinary skill in the art.

As used herein, "fluorescent responsive antibody" refers to antibodies which themselves fluoresce, or antibodies which are tagged to fluoresce under specified stimulation.

It is to be understood that the schematics of FIG. 2 are merely representative of the functional aspects of the principles of the present invention, and may be embodied in numerous alternative fashions in accordance with the routine abilities of those of ordinary skill in the art. Likewise, it is understood that the methods and apparatus set forth herein constitute preferred and illustrative embodiments of the principles of the present invention, but that numerous alternatives will occur to those of ordinary skill in the art without departure from the spirit or scope of the present invention.

EXAMPLE

Material and Methods:

A. Cell preparation

Whole blood from normal human donors was anticoagulated with EDTA. The buffy coat was removed and the concentration of leukocytes in the buffy coat was determined. The percentage of lymphocytes was estimated on a modified Cytofluorograph (Ortho Instruments, Westwood, MA) as described below. If the lymphocyte concentration was greater than 10,000/mm$^3$ the buffy coat was diluted with phosphate-buffered saline (i.e. "PBS") (Dulbeco) to a concentration of 10,000 lymphocytes/mm$^3$.

B. Indirect Immunofluorescent staining.

100 $\mu$l of buffy coat was incubated with 100 $\mu$l of appropriately diluted monoclonal antibody (mouse-antilymphocyte subclass) at 4° C. for 30 min. At the end of this incubation the cells were treated with 2-4 ml of buffered, isotonic ammonium chloride (NH$_4$Cl 16.58 g/l, disodium EDTA, 0.074 g/l, potassium bicarbonate 2.00 g/l, pH=7.3). After five minutes the red cells had lysed, and the suspension was centrifuged at 200$\times$G for five minutes. The supernate was removed, and the pellet containing the leukocytes and residual platelets and red cell ghosts was washed once in PBS. The pellet was gently dispersed and incubated at 4° C. for 30 minutes with 100 $\mu$l of a 40:1 dilution of fluorescinated goat-anti-mouse 7S (Meloy Laboratories, Springfield, VA) F/p=2.5. After this incubation, and optional further washes with PBS, the cells were diluted to a final volume of 1 ml. and were ready for analysis on the flow cytometer.

C. Flow Cytometric Analysis

A Cytofluorograph FC200/4800A (Ortho Instruments, Westwood, MA) was used simultaneously to measure the forward and right angle light scatter and the green fluorescein fluorescence of each cell in the sample. The instrument was modified by replacing the "red" filter block with filters appropriate for directing the blue laser light scattered at right angles to the incident beam into the photomultiplier normally used to detect red fluorescence. The green filter block contained an FITC filter. The right angle scatter signal along with the normally available forward scatter signal were displayed as a cytogram on the 4800A analyzer. By using the controls on the instrument a gate pulse was produced for cells having particular combinations of forward and right angle light scatter. The green fluorescence pulses were electrically integrated by a separate module added to the 4800A, and the integrated fluorescence pulses were recorded on a pulse height analyzer (Model 2102, Ortho Instruments, Westwood, MA). By using the gate pulse from the 4800A it was possible to record fluorescence pulses from only those cells with particular light scattering properties.

D. Results

Figure 3A:
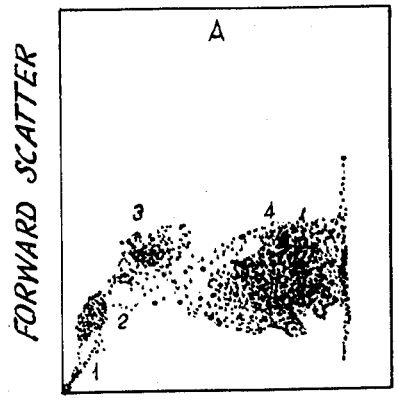
FIGS. 3A through 3F shows histograms which illustrate application of the principles of the present invention.
Figure 3B:
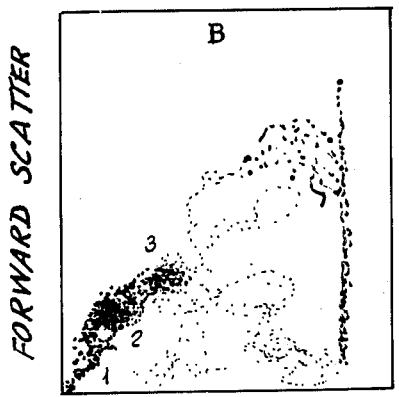

The method of leukocyte identification is illustrated in the cytograms in FIGS. 3A and 3B. As used herein, the term "cytogram" is a representation of data, wherein each dot represents a single cell, and the location of the dot is given by coordinates which are proportional to selected parameters, for example to the right angle and forward light scatter intensities produced by the cell in the Cytofluorograph. The sample in FIG. 3A was whole blood diluted with the ammonium chloride lysing reagent. Four clusters of dots or cells can be distinguished. Cluster 1 is due to aggregates or multiplets of platelets and red cell ghosts. Clusters 2-4 are due to lymphocytes, monocytes and granulocytes respectively. The identification of the leukocyte clusters is based on the comparison of the relative number of counts in each cluster with manual differential leukocyte counts. Similar clusters were observed with a red (HeNe) laser on a prototype cell sorter. Sorting of the cells in the corresponding clusters, staining the cells with acridine orange and observing the cells under a fluorescent microscope provided additional evidence that the clusters were correctly identified. FIG. 3B is the cytogram of a sample of "mononuclear cells" prepared by density gradient separation of whole blood. The platelet aggregate, lymphocyte and monocyte clusters are similar to those in FIG. 3A, while the granulocyte cluster is absent, as expected. It is evident from FIGS. 3A and 3B that the lymphocytes are readily distinguished from granulocytes. There may be a small amount of overlap of lymphocytes and monocytes in clusters 2 and 3, but for present purposes it has seemed sufficient to take cluster 2 as containing only lymphocytes and cluster 3 as containing only monocytes.

Figure 3C:
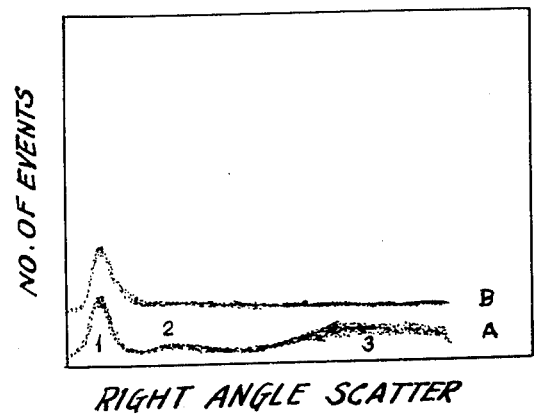

Forward light scatter is seen from FIGS. 3A and 3B to be primarily useful in discriminating the leukocytes from platelets and red cell ghosts. The instrumental threshold was typically set to exclude these smaller cells so that only leukocytes are counted. When this is done the right angle light scatter parameter alone provides excellent discrimination of the leukocyte types. Histograms "A" and "B" in FIG. 3C, correspond to the cytograms shown in FIGS. 3A and 3B respectively. Peaks 1 through 3 correspond to lymphocytes, monocytes and granulocytes, respectively.

Figure 3D:
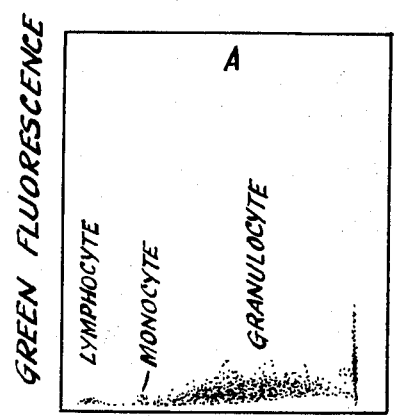
Figure 3E:
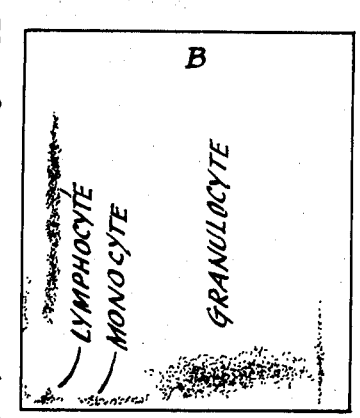

When the immunofluorescent staining procedure is applied to buffy coat the final cell preparation produces light scattering clusters essentially the same as those shown in FIG. 3A. Since lymphocytes, monocytes and granulocytes can be distinguished on the basis of right angle light scattering, a cytogram of green fluorescence vs. right angle scatter will show which of these leukocyte types is stained. FIGS. 3D and 3E show such cytograms for blood samples incubated with a control, FIG. 3D, or anit-T cell, FIG. 3E, antibody. The control was a supernate from a non-antibody producing clone while the anti-T cell antibody was a monoclonal antibody. In the case of the control, only granulocytes showed significant fluorescence.

Blood stained with the anti-T antibody, however, showed a distinct lymphocyte cluster that had relatively intense fluorescence. This "T" cluster contained 77% of the lymphocytes (as defined by light scatter) and apparently contains only T-lymphocytes.

Figure 3F:
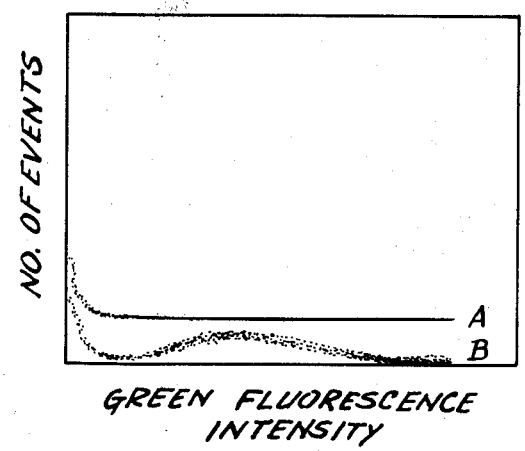

FIG. 3F shows histograms of green fluorescence from the lymphocyte cluster (cluster 2 in FIG. 3A). Histogram A of FIG. 3F is for the sample with control antibody, while histogram B of FIG. 3F is for the sample with the anti-T antibody. The T cells produce a distinct peak in histogram B of FIG. 3F. The T cells form a very distinct peak. A histogram of green fluorescence from all the leukocytes has a peak due to granulocytes that partially overlaps the T-lymphocyte peak.

Experiments with several different lymphocyte-subclass specific antibodies using blood from several human donors have given results of a quality similar to that reported above. Blood tested with antibodies characterized as anti-T cell typically had 70%-80% of cells in the lymphocyte cluster produces significant fluorescence. Blood tested with antibodies characterized as anti-B cell typically had 20% of cells in the lymphocyte cluster produce significant fluorescence. These results are in the normal range of T-cell and B-cell percentages.

What is claimed is:

1. An automated method of identifying and enumerating cells of a select subclass of lymphocytes in blood comprising the steps of:
   (a) providing an aliquot from the blood to be studied;
   (b) selectively tagging cells of said subclass by incubating said aliquot with an antibody which is selectively reactive with distinct antigenic determinants on the surface of cells of said subclass, said antibody having a predetermined fluorescence response to a given optical stimulation;
   (c) lysing red cells from said aliquot;
   (d) passing said aliquot, substantially a cell at a time, through an area of focused optical stimulation of said given type, while detecting light scattered by and emitted from said cells; and
   (e) differentiating cells of said subclass based at least in part on occurrence of said predetermined fluorescence response in said detected light.

2. A method as defined in claim 1 wherein said providing step comprises providing anticoagulated but otherwise substantially unprocessed whole blood.

3. A method as defined in claim 1 wherein said providing step comprises providing a sample of whole blood, centrifuging said sample for a predetermined period of time, isolating the buffy coat layer from said sample, and providing said isolated buffy coat layer as said aliquot.

4. A method as described in claim 1, adapted for identification and enumeration of specified subclasses of T-type lymphocytes, wherein said tagging step comprises incubating said aliquot with anti-said subclass antibody which fluoresces within known intensity and frequency ranges when irradiated by optical stimulation of given wavelengths.

5. A method as described in claim 4, wherein said passing step comprises providing the focus of an argon laser at said area.

6. A method as described in claim 1, wherein said passing step further comprises:
   providing respective reference ranges for forward light scatter and right angle scatter;
   detecting forward and right angle scatter pulses for a given cell;
   comparing respective detected pulses with corresponding reference ranges;
   enabling, when both said detected pulses are within their said corresponding ranges, detection of right angle fluorescence of said predetermined response.

7. A method as described in claims 1 or 4 wherein said tagging step comprises incubating said aliquot with a quantity of said antibody which has previously been associated with a fluorescing dye agent.

8. A method as described in claims 1 or 4 wherein said tagging step comprises first incubating said aliquot with a nonfluorescently responsive antibody, then further incubating said aliquot with an antibody reagent which has said predetermined fluorescence response and which is reactive with nonfluorescently responsive antibody.

9. Apparatus for identification and enumeration of specified T-lymphocytes in a sample which has been incubated with a fluorescent responsive antibody to select antigenic determinant on the surface of said specified T-lymphocytes comprising:
   (a) a flow cytometry flow cell for passing cells of said sample, rapidly and substantially one at a time, through a given area;
   (b) a source of light which stimulates fluorescence in said antibody;
   (c) means for coupling and focusing light from said source to cell flow at said given area;
   (d) first photosensing means for detecting forward light scatter from said means for coupling and dispersed from said area by a cell passing therethrough;
   (e) second photosensing means for detecting light scattered by said cell on an axis substantially normal to the axis of cell flow;
   (f) third photosensing means, for sensing fluorescent light pulses;
   (g) means for providing respective reference ranges for forward light scatter and right angle light scatter;
   (h) means for comparing light pulses detected by said first and second photosensing means with associated ranges from means for providing; and
   (i) means, responsive to said means for providing, for selectively enabling said third photosensing means when said detected light pulses occur within associated reference ranges; and
   (j) means for displaying fluorescent light pulses as indicia of occurrence of said specified T-lymphocyte cells at said area.

10. Apparatus as described in claim 9 and further including means, responsive to said means for selectively enabling, for compensating signals detected by said third photosensing means to account for preselected spurious fluorescence effect, said means for displaying being responsive in turn to said means for compensating.

11. Apparatus as described in claim 9 wherein said means for coupling and focusing is arranged to deliver light from said source substantially orthogonally to cell flow at said given area.

12. Apparatus as described in claim 9 wherein said source of light comprises an argon ion laser, and wherein said third photosensing means comprises means for sensing green fluorescent light pulses.

13. Apparatus as described in claim 12 wherein said third photosensing means is adapted to sense said green light pulses along said normal axis.

14. Apparatus for identification and enumeration of a specified subclass of blood cells in a sample which has been incubated with a fluorescent responsive antibody to a select antigenic determinant on the surface of said specified subclass of blood cells comprising:
 (a) a flow cytometry flow cell for passing cells of said sample, rapidly and substantially one at a time, through a given area;
 (b) a source of light which stimulates fluorescence in said antibody;
 (c) means for coupling and focusing light from said source to cell flow at said given area;
 (d) first photosensing means for detecting forward light scatter from said means for coupling and dispersed from said area by a cell passing therethrough;
 (e) second photosensing means for detecting light scattered by said cell on an axis substantially normal to the axis of cell flow;
 (f) third photosensing means, for sensing fluorescent light pulses;
 (g) means for providing respective reference ranges for forward light scatter and right angle light scatter;
 (h) means for comparing light pulses detected by said first and second photosensing means with associated ranges from means for providing; and
 (i) means, responsive to said means for providing, for selectively enabling said third photosensing means when said detected light pulses occur within associated reference ranges; and
 (j) means for displaying fluorescent light pulses as indicia of occurrence of said specified subclass of blood cells at said area.

* * * * *